(12) United States Patent
Uchiyama et al.

(10) Patent No.: US 9,970,946 B2
(45) Date of Patent: May 15, 2018

(54) MARKER PEPTIDE FOR DETERMINING RISK OF HYPERGLYCEMIA AND USE THEREOF

(71) Applicant: LION CORPORATION, Sumida-ku (JP)

(72) Inventors: Chiyoko Uchiyama, Tokyo (JP); Kei Kurita, Tokyo (JP)

(73) Assignee: LION CORPORATION, Sumida-ku (JP)

( * ) Notice: Subject to any disclaimer, the term of this patent is extended or adjusted under 35 U.S.C. 154(b) by 204 days.

(21) Appl. No.: 14/438,479

(22) PCT Filed: Dec. 10, 2013

(86) PCT No.: PCT/JP2013/083118
§ 371 (c)(1),
(2) Date: Apr. 24, 2015

(87) PCT Pub. No.: WO2014/097932
PCT Pub. Date: Jun. 26, 2014

(65) Prior Publication Data
US 2015/0285821 A1    Oct. 8, 2015

(30) Foreign Application Priority Data

Dec. 20, 2012  (JP) ................................ 2012-278388

(51) Int. Cl.
*G01N 33/68* (2006.01)
*C07K 14/47* (2006.01)

(52) U.S. Cl.
CPC ......... *G01N 33/6893* (2013.01); *C07K 14/47* (2013.01); *G01N 33/68* (2013.01);
(Continued)

(58) Field of Classification Search
CPC ............. G01N 33/68; G01N 2800/042; G01N 2333/47; G01N 2333/8139
See application file for complete search history.

(56) References Cited

U.S. PATENT DOCUMENTS 7,812,128 B2 * 10/2010 Aburatani .............. C07K 14/47
530/350
7,914,460 B2 * 3/2011 Melker .................. A61B 5/083
600/365
(Continued)

FOREIGN PATENT DOCUMENTS

| CN | 1928557 A | 3/2007 |
|---|---|---|
| JP | 2003-177125 A | 6/2003 |
| JP | 2011-515680 A | 5/2011 |
| JP | 2012-507020 A | 3/2012 |
| WO | 2006/064844 A1 | 6/2006 |
| WO | 2013/108561 A1 | 7/2013 |

OTHER PUBLICATIONS

Tiziana Cabras, et al., "Alterations of the Salivary Secretory Peptidome Profile in Children Affected by Type 1 Diabetes", Molecular & Cellular Proteomics, vol. 9, No. 10, pp. 2099-2108, (2009).

(Continued)

*Primary Examiner* — Jeffrey E. Russel
(74) *Attorney, Agent, or Firm* — Oblon, McClelland, Maier & Neustadt, L.L.P.

(57) ABSTRACT

The object of the present invention is to provide a marker substance capable of determining a risk of hyperglycemia in vivo with high accuracy. The present invention provides the following: a marker peptide for determining the risk of hyperglycemia; an antibody or an aptamer bound to the marker peptide for determining the risk of hyperglycemia; a microarray wherein the antibody or the aptamer to be bound to the marker peptide for determining the risk of hyperglycemia has been immobilized onto a carrier; a method of determining the risk of hyperglycemia wherein an amount or the presence/absence of the marker peptide for determining (Continued)

the risk of hyperglycemia is measured in a biological sample collected from a subject; and a kit for determining the risk of hyperglycemia comprising the antibody or the aptamer, or the microarray.

10 Claims, 2 Drawing Sheets

(52) U.S. Cl.
CPC . *G01N 2333/47* (2013.01); *G01N 2333/8139* (2013.01); *G01N 2800/042* (2013.01); *G01N 2800/50* (2013.01)

(56) References Cited

U.S. PATENT DOCUMENTS

| | | |
|---|---|---|
| 2004/0241774 A1 | 12/2004 | Kazuo |
| 2010/0015146 A1* | 1/2010 | Lau .................... C07K 14/7155 424/136.1 |
| 2010/0041167 A1 | 2/2010 | Aburatani et al. |
| 2010/0331278 A1* | 12/2010 | Anderson ................. A23L 2/52 514/57 |
| 2011/0250618 A1 | 10/2011 | Nelson et al. |
| 2011/0318766 A1 | 12/2011 | Struck et al. |
| 2015/0160239 A1 | 6/2015 | Uchiyama et al. |

OTHER PUBLICATIONS

Maija I. Mednieks, et al., "Protein expression in salivary glands of rats with streptozotocin diabetes", International Journal of Experimental Pathology, vol. 90, pp. 412-422, (2009).

International Search Report dated Jan. 14, 2014 in PCT/JP13/083118 Filed Dec. 10, 2013.

U.S. Appl. No. 14/371,655, filed Jul. 10, 2014, US2015/0160239 A1, Uchiyama, et al.

Japanese Office Action dated May 17, 2016 in Patent Application No. 2012-278388 (with English language translation).

Christophe Hirtz, et al., "Salivary Protein Profiling in Type I Diabetes Using Two-Dimensional Electrophoresis and Mass Spectrometry" Clinical Proteomics, vol. 2, 2006, pp. 117-127.

Combined Chinese Office Action and Search Report dated Apr. 5, 2017 in Patent Application No. 201380066714.6 (with partial English translation and English translation of categories of cited documents).

Strausberg, R. L., "UniProtKB-P01037 (CYTN_HUMAN)" Uni Prot, Nov. 2, 2010, 3 Pages.

Kim, H. S., "UniProtKB-P04280 (PRP1_HUMAN)" Uni Prot, Sep. 13, 2004, 4 Pages.

Maeda, N., "UniProtKB-P02812 (PRB2_HUMAN)" Uni Prot, Oct. 23, 2007, 3 Pages.

* cited by examiner

SEQUENCE LISTING

```
<160> NUMBER OF SEQ ID NOS: 3

<210> SEQ ID NO 1
<211> LENGTH: 141
<212> TYPE: PRT
<213> ORGANISM: Homo sapiens

<400> SEQUENCE: 1

Met Ala Gln Tyr Leu Ser Thr Leu Leu Leu Leu Ala Thr Leu Ala
1               5                   10                  15

Val Ala Leu Ala Trp Ser Pro Lys Glu Glu Asp Arg Ile Ile Pro Gly
                20                  25                  30

Gly Ile Tyr Asn Ala Asp Leu Asn Asp Glu Trp Val Gln Arg Ala Leu
            35                  40                  45

His Phe Ala Ile Ser Glu Tyr Asn Lys Ala Thr Lys Asp Asp Tyr Tyr
        50                  55                  60

Arg Arg Pro Leu Arg Val Leu Arg Ala Arg Gln Gln Thr Val Gly Gly
65                  70                  75                  80

Val Asn Tyr Phe Phe Asp Val Glu Val Gly Arg Thr Ile Cys Thr Lys
                85                  90                  95

Ser Gln Pro Asn Leu Asp Thr Cys Ala Phe His Glu Gln Pro Glu Leu
                100                 105                 110

Gln Lys Lys Gln Leu Cys Ser Phe Glu Ile Tyr Glu Val Pro Trp Glu
            115                 120                 125

Asn Arg Arg Ser Leu Val Lys Ser Arg Cys Gln Glu Ser
        130                 135                 140

<210> SEQ ID NO 2
<211> LENGTH: 416
<212> TYPE: PRT
<213> ORGANISM: Homo sapiens

<400> SEQUENCE: 2

Met Leu Leu Ile Leu Leu Ser Val Ala Leu Leu Ala Leu Ser Ser Ala
1               5                   10                  15

Gln Asn Leu Asn Glu Asp Val Ser Gln Glu Glu Ser Pro Ser Leu Ile
                20                  25                  30

Ala Gly Asn Pro Gln Gly Ala Pro Pro Gln Gly Gly Asn Lys Pro Gln
```

```
                35                  40                  45
Gly Pro Pro Ser Pro Pro Gly Lys Pro Gln Gly Pro Pro Gln Gly
 50                  55                  60

Gly Asn Gln Pro Gln Gly Pro Pro Pro Gly Lys Pro Gln Gly
 65                  70                  75                  80

Pro Pro Pro Gln Gly Asn Lys Pro Gln Gly Pro Pro Pro Gly
                 85                  90                  95

Lys Pro Gln Gly Pro Pro Gln Gly Asp Lys Ser Arg Ser Pro Arg
                100                 105                 110

Ser Pro Pro Gly Lys Pro Gln Gly Pro Pro Gln Gly Gly Asn Gln
                115                 120                 125

Pro Gln Gly Pro Pro Pro Pro Gly Lys Pro Gln Gly Pro Pro Pro
130                 135                 140

Gln Gly Gly Asn Lys Pro Gln Gly Pro Pro Pro Gly Lys Pro Gln
145                 150                 155                 160

Gly Pro Pro Pro Gln Gly Asp Asn Lys Ser Arg Ser Arg Ser Pro
                165                 170                 175

Pro Gly Lys Pro Gln Gly Pro Pro Gln Gly Gly Asn Gln Pro Gln
                180                 185                 190

Gly Pro Pro Pro Pro Gly Lys Pro Gln Gly Pro Pro Pro Gln Gly
                195                 200                 205

Gly Asn Lys Pro Gln Gly Pro Pro Pro Gly Lys Pro Gln Gly Pro
210                 215                 220

Pro Pro Gln Gly Asp Asn Lys Ser Gln Ser Ala Arg Ser Pro Pro Gly
225                 230                 235                 240

Lys Pro Gln Gly Pro Pro Gln Gly Gly Asn Gln Pro Gln Gly Pro
                245                 250                 255

Pro Pro Pro Gly Lys Pro Gln Gly Pro Pro Pro Gln Gly Gly Asn
                260                 265                 270

Lys Ser Gln Gly Pro Pro Pro Gly Lys Pro Gln Gly Pro Pro Pro
                275                 280                 285

Gln Gly Gly Ser Lys Ser Arg Ser Ser Arg Ser Pro Pro Gly Lys Pro
290                 295                 300

Gln Gly Pro Pro Pro Gln Gly Gly Asn Gln Pro Gln Gly Pro Pro Pro
305                 310                 315                 320

Pro Pro Gly Lys Pro Gln Gly Pro Pro Gln Gly Gly Asn Lys Pro
                325                 330                 335

Gln Gly Pro Pro Pro Gly Lys Pro Gln Gly Pro Pro Gln Gly
                340                 345                 350

Gly Ser Lys Ser Arg Ser Ala Arg Ser Pro Gly Lys Pro Gln Gly
                355                 360                 365

Pro Pro Gln Gln Glu Gly Asn Pro Gln Gly Pro Pro Pro Ala
                370                 375                 380

Gly Gly Asn Pro Gln Gln Pro Gln Ala Pro Ala Gly Gln Pro Gln
385                 390                 395                 400

Gly Pro Pro Arg Pro Pro Gln Gly Gly Arg Pro Ser Arg Pro Pro Gln
                405                 410                 415
```

<210> SEQ ID NO 3
<211> LENGTH: 392
<212> TYPE: PRT
<213> ORGANISM: Homo sapiens

<400> SEQUENCE: 3

```
Met Leu Leu Ile Leu Leu Ser Val Ala Leu Ala Leu Ser Ser Ala
1               5                   10                  15

Gln Asn Leu Asn Glu Asp Val Ser Gln Glu Glu Ser Pro Ser Leu Ile
            20                  25                  30

Ala Gly Asn Pro Gln Gly Pro Ser Pro Gln Gly Gly Asn Lys Pro Gln
            35                  40                  45

Gly Pro Pro Pro Pro Pro Gly Lys Pro Gln Gly Pro Pro Pro Gln Gly
50                      55                  60

Gly Asn Lys Pro Gln Gly Pro Pro Pro Gly Lys Pro Gln Gly Pro
65                  70                  75                  80

Pro Pro Gln Gly Asp Lys Ser Arg Ser Pro Arg Ser Pro Pro Gly Lys
                85                  90                  95

Pro Gln Gly Pro Pro Pro Gln Gly Gly Asn Gln Pro Gln Gly Pro Pro
                100                 105                 110

Pro Pro Pro Gly Lys Pro Gln Gly Pro Pro Pro Gln Gly Gly Asn Lys
            115                 120                 125

Pro Gln Gly Pro Pro Pro Gly Lys Pro Gln Gly Pro Pro Pro Gln
    130                 135                 140

Gly Asp Lys Ser Gln Ser Pro Arg Ser Pro Pro Gly Lys Pro Gln Gly
145                 150                 155                 160

Pro Pro Pro Gln Gly Gly Asn Gln Pro Gln Gly Pro Pro Pro Pro Pro
                165                 170                 175

Gly Lys Pro Gln Gly Pro Pro Gln Gly Gly Asn Lys Pro Gln Gly
            180                 185                 190

Pro Pro Pro Pro Gly Lys Pro Gln Gly Pro Pro Pro Gln Gly Asp Lys
                195                 200                 205

Ser Gln Ser Pro Arg Ser Pro Pro Gly Lys Pro Gln Gly Pro Pro Pro
    210                 215                 220

Gln Gly Gly Asn Gln Pro Gln Gly Pro Pro Pro Pro Pro Gly Lys Pro
225                 230                 235                 240

Gln Gly Pro Pro Gln Gly Gly Asn Arg Pro Gln Gly Pro Pro Pro
            245                 250                 255

Pro Gly Lys Pro Gln Gly Pro Pro Pro Gln Gly Asp Lys Ser Arg Ser
            260                 265                 270

Pro Gln Ser Pro Pro Gly Lys Pro Gln Gly Pro Pro Pro Gln Gly Gly
    275                 280                 285

Asn Gln Pro Gln Gly Pro Pro Pro Pro Gly Lys Pro Gln Gly Pro
    290                 295                 300

Pro Pro Gln Gly Gly Asn Lys Pro Gln Gly Pro Pro Pro Pro Gly Lys
305                 310                 315                 320

Pro Gln Gly Pro Pro Ala Gln Gly Gly Ser Lys Ser Gln Ser Ala Arg
            325                 330                 335

Ala Pro Pro Gly Lys Pro Gln Gly Pro Pro Gln Gln Glu Gly Asn Asn
            340                 345                 350

Pro Gln Gly Pro Pro Pro Ala Gly Gly Asn Pro Gln Gln Pro Gln
    355                 360                 365

Ala Pro Pro Ala Gly Gln Pro Gln Gly Pro Pro Arg Pro Pro Gln Gly
    370                 375                 380

Gly Arg Pro Ser Arg Pro Pro Gln
385                 390
```

MARKER PEPTIDE FOR DETERMINING RISK OF HYPERGLYCEMIA AND USE THEREOF

TECHNICAL FIELD

The present invention relates to a marker peptide for determining a risk of hyperglycemia and use thereof.

BACKGROUND ART

More than 10 million patients suffer from diabetes in Japan in 2011 and this number is the sixth largest in the world. Diabetes is a serious condition causing complications such as retinopathy and gangrene in its severe stage and having a risk of losing their life due to such a complication. It has been said that, Japanese have constitutional factors to be insensitive to consumption of what one has eaten and to be easy to accumulate them, and thus Japanese are liable to diabetes. Therefore, taking an ingenuity of how to ingest diets and/or enforcement of exercise are recommended for preventing diabetes and progress into severe disease.

A pre-diabetic condition includes a hyperglycemic condition. It is necessary at a stage of the hyperglycemic condition to regularly figure out a blood glucose level, keep a lifestyle not to increase the blood glucose level and improve a lifestyle increasing the blood glucose level. If it is possible to regularly figure out a blood glucose level by non-invasive and always-collectable specimen, self-medication at home can be achieved.

Cystatin is a set of peptide group having an antioxidant effect. Patent Literature 1 describes that cystatin-C can be used as a biomarker when diabetes is detected. Patent Literature 2 describes that cystatin-C can be used as an examination parameter for the diabetes. Patent Literature 3 describes that a diagnosis agent containing an anti-cystatin-SN antibody for colorectal cancer and/or colorectal polyp has been described in. Cystatin-C is present abundantly in semen and spinal fluid and present in only a small amount in saliva. Meanwhile, cystatin-SN is present mainly in saliva and tears.

Basic salivary proline-rich protein 1 and basic salivary proline-rich protein 2 are one type of proline-rich proteins (proline-rich peptides) comprising a proline-rich non-periodically amino acid sequence moiety. Non-Patent Literature 1 describes that the expression of the proline-rich peptide in salivary grands in diabetes model rats was decreased compared with that in the control group and the decreased expression of the proline-rich peptide in the diabetes model rats was improved by administration of insulin.

CITATION LIST

Patent Literatures

Patent Literature 1: JP unexamined patent application Publication No. 2011-515680
Patent Literature 2: JP unexamined patent application Publication No. 2012-507020
Patent Literature 3: International Publication WO06/064844

Non-Patent Literatures

Non-Patent Literature 1: Int. J. Exp. Path., 90, 412-422

SUMMARY OF INVENTION

Problem to be Solved by the Invention

However, neither a marker peptide capable of accurately detecting a risk of hyperglycemia irrespective of a sampling site and also in saliva nor a method of detecting the risk of hyperglycemia using the same is not known so far. Also, it has not been known so far that cystatin-SN, basic salivary proline-rich protein 1 and basic salivary proline-rich protein 2 are associated with hyperglycemia. A homology score of cystatin-SN to cystatin-C is only 54.6099. Thus, cystatin-SN can be said to be largely different in structure from cystatin-C.

The object of the present invention is to provide a marker substance capable of determining a risk of hyperglycemia in vivo with high accuracy.

Means for Solving Problem

The present invention provides the following [1] to [10].
[1] A marker peptide for determining a risk of hyperglycemia that is selected from the group consisting of (A) to (O):
(A) a polypeptide comprising 5 or more consecutive amino acid residues in the amino acid sequence of SEQ ID NO:1;
(B) a polypeptide comprising an amino acid sequence having one or several amino acid deletions, additions, substitutions or insertions in 5 or more consecutive amino acid residues in the amino acid sequence of SEQ ID NO:1, and capable of being used as a marker for determining the risk of hyperglycemia;
(C) a polypeptide comprising an amino acid sequence having 90% or more homology to 5 or more consecutive amino acid residues in the amino acid sequence of SEQ ID NO:1, and capable of being used as the marker for determining the risk of hyperglycemia;
(D) a polypeptide comprising 5 or more consecutive amino acid residues in an amino acid sequence having one or several amino acid deletions, additions, substitutions or insertions in the amino acid sequence of SEQ ID NO:1, and capable of being used as the marker for determining the risk of hyperglycemia;
(E) a polypeptide comprising 5 or more consecutive amino acid residues in an amino acid sequence having 90% or more homology to the amino acid sequence of SEQ ID NO:1, and capable of being used as the marker for determining the risk of hyperglycemia;
(F) a polypeptide comprising 5 or more consecutive amino acid residues in the amino acid sequence of SEQ ID NO:2;
(G) a polypeptide comprising an amino acid sequence having one or several amino acid deletions, additions, substitutions or insertions in 5 or more consecutive amino acid residues in the amino acid sequence of SEQ ID NO:2, and capable of being used as a marker for determining a risk of hyperglycemia;
(H) a polypeptide comprising an amino acid sequence having 90% or more homology to 5 or more consecutive amino acid residues in the amino acid sequence of SEQ ID NO:2, and capable of being used as the marker for determining the risk of hyperglycemia;
(I) a polypeptide comprising 5 or more consecutive amino acid residues in an amino acid sequence having one or several amino acid deletions, additions, substitutions or insertions in the amino acid sequence of SEQ ID NO:2, and capable of being used as the marker for determining the risk of hyperglycemia;

(J) a polypeptide comprising 5 or more consecutive amino acid residues in an amino acid sequence having 90% or more homology to the amino acid sequence of SEQ ID NO:2, and capable of being used as the marker for determining the risk of hyperglycemia;

(K) a polypeptide comprising 5 or more consecutive amino acid residues in the amino acid sequence of SEQ ID NO:3;

(L) a polypeptide comprising an amino acid sequence having one or several amino acid deletions, additions, substitutions or insertions in 5 or more consecutive amino acid residues in the amino acid sequence of SEQ ID NO:3, and capable of being used as the marker for determining the risk of hyperglycemia;

(M) a polypeptide comprising an amino acid sequence having 90% or more homology to 5 or more consecutive amino acid residues in the amino acid sequence of SEQ ID NO:3, and capable of being used as the marker for determining the risk of hyperglycemia;

(N) a polypeptide comprising 5 or more consecutive amino acid residues in an amino acid sequence having one or several amino acid deletions, additions, substitutions or insertions in the amino acid sequence of SEQ ID NO:3, and capable of being used as the marker for determining the risk of hyperglycemia; and (O) a polypeptide comprising 5 or more consecutive amino acid residues in an amino acid sequence having 90% or more homology to the amino acid sequence of SEQ ID NO:3, and capable of being used as the marker for determining the risk of hyperglycemia.

[2] An antibody or an aptamer bound to the marker peptide for determining the risk of hyperglycemia according to [1].

[3] A microarray wherein an antibody or an aptamer to be bound to the marker peptide for determining the risk of hyperglycemia according to [1] has been immobilized on a carrier.

[4] A method of determining a risk of hyperglycemia, wherein an amount or the presence/absence of the marker peptide for determining the risk of hyperglycemia according to [1] is measured in a biological sample collected from a subject.

[5] The method of determining the risk of hyperglycemia according to [4], wherein the risk of hyperglycemia is determined to be high when an amount of the marker peptide for determining the risk of hyperglycemia according to [1] is smaller than the amount of the marker peptide in a biological sample collected from a healthy donor.

[6] The method of determining the risk of hyperglycemia according to [4], wherein the risk of hyperglycemia is determined to be high when an amount of the marker peptide for determining the risk of hyperglycemia according to [1] is equivalent to or smaller than the amount of the marker peptide in a biological sample collected from a donor with hyperglycemia.

[7] The method according to any one of [4] to [6], in which the marker peptide for determining the risk of hyperglycemia according to [1] is measured by a method selected from: a mass spectrometry; an immunoassay using the antibody or the aptamer according to [2]; and an immunoassay using the microarray according to [3].

[8] The method according to any one of [4] to [7], wherein the biological sample is saliva.

[9] A kit for determining a risk of hyperglycemia comprising the antibody or the aptamer according to [2] or the microarray according to [3].

[10] The kit according to [9] further comprising a gum.

Effect of the Invention

According to the present invention, the risk of hyperglycemia can be determined with high accuracy. If the risk of hyperglycemia is determined by utilizing the present invention prior to diagnosis by a physician, prevention measures can be taken early, development of a disease such as hyperglycemia and diabetes can be prevented before the disease occurs, and the determination of the risk is useful for keeping health.

DESCRIPTION OF EMBODIMENTS

Figure 1:
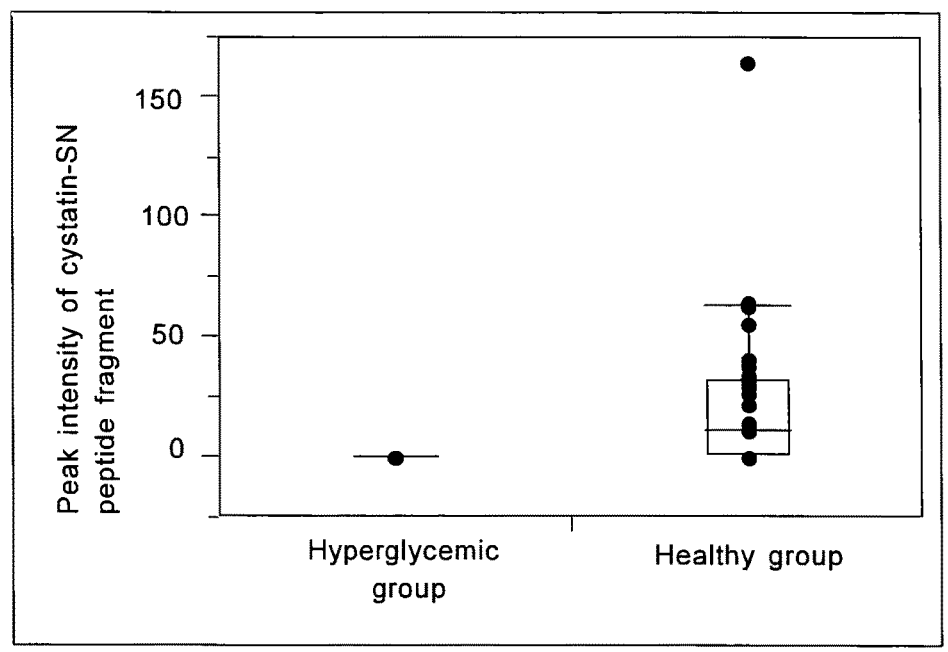
FIG. 1 indicates peak intensity of a cystatin-SN peptide fragment in each subject group.

In the present invention, determination of a risk of hyperglycemia means determining (evaluating, discriminating, differentiating, estimating) whether a subject has a hyperglycemic state or not, or has been already back to a normal level or not, or has a possibility to become hyperglycemic in future or not, or distinguishing (classifying) whether the subject has a possibility to have the risk of hyperglycemia or not. The determination of the risk of hyperglycemia means determination of whether a subject has the hyperglycemic state or not, or has been already back to the normal level or not, or has the possibility to become hyperglycemic in future or not. An accuracy of the determination of the risk of hyperglycemia is an extent that the risk of hyperglycemia can correctly be determined generally in subjects in statistically significant ratio of subjects in subjects, and for example, an extent that the risk of hyperglycemia can correctly be determined in 50% or more, 60% or more, 70% or more, 80% or more, 85% or more, or 90% or more subjects. The determination method of the present invention is useful as a preliminary determination method prior to diagnosis by a physician.

A hyperglycemic state in the present invention refers to a state where a fasting blood glucose level is 110 mg/dL or more and/or a hemoglobin A1c level is 5.8% or more.

The subject in the present invention is generally an animal, preferably a human or an experimental animal such as mouse, rat, guinea pig, hamster, rabbit, and more preferably a human.

(1) Marker Peptide of the Present Invention

A marker peptide for determining the risk of hyperglycemia of the present invention is one or more selected from the group consisting of (A) to (O) above. The peptide of the present invention is useful as the marker for determining the risk of hyperglycemia.

When the risk of hyperglycemia is determined using the marker peptide for determining the risk of hyperglycemia of the present invention, one type selected from (A) to (O) may be used, but more highly accurate determination is possible by combining two or more selected from (A) to (O). In the combination of two or more, it is preferable to combine two or more selected from one or more peptides selected from (A) to (E), one or more peptides selected from (F) to (J), and one or more peptides selected from (K) to (O).

(1-1) Concerning (A) to (C)

In (A) to (C), the amino acid sequence of SEQ ID NO:1 is an amino acid sequence encoding a human cystatin-SN peptide (full length 141 amino acids) and has been registered as the accession number P01037.3 in the database. A homology score of cystatin-SN to other types of cystatin included in a cystatin family is low as follows: cystatin-C (54.6099%), cystatin-M (27.6596%), cystatin-E (27.6596%), cystatin-F (26.2411%), cystatin-A (17.3469%) and cystatin-B (14.2857%) (the numbers in parentheses denote the homology score). The above homology scores are the values calculated by inputting the amino acid sequences to Multiple Sequence Alignment by CLUSTALW.

In (A) to (C), 5 or more consecutive amino acid residues in the amino acid sequence of SEQ ID NO:1 are preferably 7 or more consecutive amino acid residues, more preferably 10 or more consecutive amino acid residues, still preferably 12 or more consecutive amino acid residues, still more preferably 14 or more consecutive amino acid residues, and particularly preferably 15 or more consecutive amino acid residues, in the amino acid sequence of SEQ ID NO:1. Its upper limit is not particularly limited, and its length may be the full length of the amino acid sequence of SEQ ID NO:1 (141 residues) or may exceed this, but is, for example, 200 or less, 100 or less, 90 or less, 80 or less, 70 or less, 60 or less, 50 or less, 40 or less, 30 or less, or 20 or less.

In (A) to (C), the 5 or more consecutive amino acid residues in the amino acid sequence of SEQ ID NO:1 preferably include at least a portion of the amino acid residues at positions 25 to 39 in SEQ ID NO:1, and more preferably, the 5 or more consecutive amino acid residues correspond to 5 or more consecutive amino acid residues in the amino acid residues at positions 25 to 39 in SEQ ID NO:1. It is preferable that the 5 or more consecutive amino acid residues correspond to the amino acid sequence of the amino acid residues at positions 25 to 39 in SEQ ID NO:1, or the amino acid sequence of SEQ ID NO:1.

(A) may be a polypeptide comprising 5 or more consecutive amino acid residues in the amino acid sequence of SEQ ID NO:1, and is preferably a polypeptide consisting of the 5 or more consecutive amino acid residues in the amino acid sequence of SEQ ID NO:1.

(B) may be a polypeptide comprising an amino acid sequence having one or several amino acid deletions, additions, substitutions or insertions in 5 or more consecutive amino acid residues in the amino acid sequence of SEQ ID NO:1 and capable of being used as a marker for determining a risk of hyperglycemia. (B) is preferably a polypeptide consisting of the amino acid sequence having one or several amino acid deletions, additions, substitutions or insertions in 5 or more consecutive amino acid residues in the amino acid sequence of SEQ ID NO:1 and capable of being used as the marker for determining the risk of hyperglycemia.

(C) may be a polypeptide comprising an amino acid sequence having 90% or more homology to 5 or more consecutive amino acid residues in the amino acid sequence of SEQ ID NO:1 and capable of being used as the marker for determining the risk of hyperglycemia. (C) is preferably a polypeptide consisting of the amino acid sequence having 90% or more homology to the 5 or more consecutive amino acid residues in the amino acid sequence of SEQ ID NO:1 and capable of being used as the marker for determining the risk of hyperglycemia.

In (B), one or several mutations of amino acid residues may be present in one region or in multiple different regions in the amino acid sequence. The term "one or several" denotes a range in which a function or a property of the marker peptide is not largely impaired. "One or several" refers to, for example, "1 to 14", "1 to 10", "1 to 7", "1 to 5", "1 to 3", "1 or 2" or "1".

A position of an amino acid residue for allowing a mutation such as deletion, addition, substitution or insertion in an amino acid sequence is obvious to a person skilled in the art. Specifically, a person skilled in the art can recognize correlativity between a structure and a function by the following procedure: (1) comparing amino acid sequences of a plurality of proteins having the same kind of activity (e.g., the amino acid sequence of SEQ ID NO:1 and the other amino acid sequence of the marker peptide for determining the risk of hyperglycemia), (2) elucidating relatively conserved regions and relatively not conserved regions, and then (3) predicting regions capable of playing an important role for the function and regions incapable of playing an important role for a function from the relatively conserved regions and the relatively not conserved regions, respectively. Therefore, a person skilled in the art can presume the position of the amino acid residue, at which the mutation is permitted in the amino acid sequence of the marker for determining the risk of hyperglycemia.

A substitution of an amino acid residue may be a conservative substitution. As used herein, the term "conservative substitution" refers to substituting a predetermined amino acid residue with an amino acid residue having a similar side chain. Families of amino acid residues having the similar side chain are well-known in the art, and examples thereof may include: amino acids having a basic side chain (e.g., lysine, arginine, histidine); amino acids having an acidic side chain (e.g., aspartic acid, glutamic acid); amino acids having non-charged polar side chain (e.g., asparagine, glutamine, serine, threonine, tyrosine, cysteine); amino acids having a nonpolar side chain (e.g., glycine, alanine, valine, leucine, isoleucine, proline, phenylalanine, methionine, tryptophan); amino acids having a branched side chain at position $\beta$ (e.g., threonine, valine, isoleucine); amino acids having an aromatic side chain (e.g., tyrosine, phenylalanine, tryptophan, histidine); amino acids having a hydroxyl group (e.g., alcoholic, phenolic)-containing side chain (e.g., serine, threonine, tyrosine); and amino acids having a sulfur-containing side chain (e.g., cysteine, methionine). Preferably, the conservative substitution of the amino acid may be the substitution between aspartic acid and glutamic acid, the substitution between arginine and lysine and histidine, the substitution between tryptophan and phenylalanine, the substitution between phenylalanine and valine, the substitution between leucine and isoleucine and alanine, or the substitution between glycine and alanine.

When used in the present invention, example of the term "homology" may include identity and similarity. The term "90% or more" is, for example, "91% or more", "92% or more", "93% or more", "94% or more", preferably "95% or more", particularly preferably "98% or more" and more preferably "99% or more".

The homology (e.g., identity, similarity) of amino acid sequences may be calculated by inputting the amino acid sequences into Multiple Sequence Alignment by CLUSTALW. The homology may also be determined using algorithm: such as BLAST (Proc. Natl. Acad. Sci. USA, 90, 5873 (1993)) by Karlin and Altschul; or FASTA (Methods Enzymol., 183, 63(1990)) by Pearson. Programs such as BLASTP and BLASTN have been developed based on BLAST. Thus, the homology of the amino acid sequences may be calculated using these programs in default setting.

Examples of (A) may include (A-1) to (A-9):

(A-1) a polypeptide consisting of 5 or more consecutive amino acid residues in the amino acid sequence of SEQ ID NO:1;

(A-2) a polypeptide comprising 5 or more consecutive amino acid residues in the amino acid sequence of SEQ ID NO:1, wherein the 5 or more consecutive amino acid residues include at least a portion of amino acid residues at positions 25 to 39 in SEQ ID NO:1;

(A-3) a polypeptide consisting of 5 or more consecutive amino acid residues in the amino acid sequence of SEQ ID NO:1, wherein the 5 or more consecutive amino acid residues include at least a portion of the amino acid residues at positions 25 to 39 in SEQ ID NO:1;

(A-4) a polypeptide comprising 5 or more consecutive amino acid residues selected from the amino acid residues at positions 25 to 39 in the amino acid sequence of SEQ ID NO:1;

(A-5) a polypeptide consisting of 5 or more consecutive amino acid residues selected from the amino acid residues at positions 25 to 39 in the amino acid sequence of SEQ ID NO:1;

(A-6) a polypeptide comprising the amino acid residues at positions 25 to 39 in the amino acid sequence of SEQ ID NO:1;

(A-7) a polypeptide consisting of the amino acid residues at positions 25 to 39 in the amino acid sequence of SEQ ID NO:1;

(A-8) a polypeptide comprising the amino acid sequence of SEQ ID NO:1; and (A-9) a polypeptide consisting of the amino acid sequence of SEQ ID NO:1.

Examples of (B) may include (B-1) to (B-9):

(B-1) a polypeptide consisting of an amino acid sequence having one or several amino acid deletions, additions, substitutions or insertions in 5 or more consecutive amino acid residues in the amino acid sequence of SEQ ID NO:1, and capable of being used as a marker for determining a risk of hyperglycemia;

(B-2) a polypeptide comprising an amino acid sequence having one or several amino acid deletions, additions, substitutions or insertions in an amino acid sequence that comprises 5 or more consecutive amino acid residues in the amino acid sequence of SEQ ID NO:1 and includes at least a portion of the amino acid residues at positions 25 to 39 in the 5 or more consecutive amino acid residues, and capable of being used as the marker for determining the risk of hyperglycemia;

(B-3) a polypeptide consisting of an amino acid sequence having one or several amino acid deletions, additions, substitutions or insertions in an amino acid sequence that comprises 5 or more consecutive amino acid residues in the amino acid sequence of SEQ ID NO:1 and includes at least a portion of the amino acid residues at positions 25 to 39 in the 5 or more consecutive amino acid residues, and capable of being used as the marker for determining the risk of hyperglycemia;

(B-4) a polypeptide comprising an amino acid sequence having one or several amino acid deletions, additions, substitutions or insertions in 5 or more consecutive amino acid residues selected from the amino acid residues at positions 25 to 39 in the amino acid sequence of SEQ ID NO:1, and capable of being used as the marker for determining the risk of hyperglycemia;

(B-5) a polypeptide consisting of an amino acid sequence having one or several amino acid deletions, additions, substitutions or insertions in 5 or more consecutive amino acid residues selected from the amino acid residues at positions 25 to 39 in the amino acid sequence of SEQ ID NO:1, and capable of being used as the marker for determining the risk of hyperglycemia;

(B-6) a polypeptide comprising an amino acid sequence having one or several amino acid deletions, additions, substitutions or insertions in the amino acid sequence of the amino acid residues at positions 25 to 39 in the amino acid sequence of SEQ ID NO:1, and capable of being used as the marker for determining the risk of hyperglycemia;

(B-7) a polypeptide consisting of an amino acid sequence having one or several amino acid deletions, additions, substitutions or insertions in the amino acid sequence of the amino acid residues at positions 25 to 39 in the amino acid sequence of SEQ ID NO:1, and capable of being used as the marker for determining the risk of hyperglycemia;

(B-8) a polypeptide comprising an amino acid sequence having one or several amino acid deletions, additions, substitutions or insertions in the amino acid sequence of SEQ ID NO:1, and capable of being used as the marker for determining the risk of hyperglycemia; and (B-9) a polypeptide consisting of an amino acid sequence having one or several amino acid deletions, additions, substitutions or insertions in the amino acid sequence of SEQ ID NO:1, and capable of being used as the marker for determining the risk of hyperglycemia.

Examples of (C) may include (C-1) to (C-9):

(C-1) a polypeptide consisting of an amino acid sequence having 90% or more homology to 5 or more consecutive amino acid residues in the amino acid sequence of SEQ ID NO:1, and capable of being used as the marker for determining the risk of hyperglycemia.

(C-2) a polypeptide comprising an amino acid sequence having 90% or more homology to an amino acid sequence that comprises 5 or more consecutive amino acid residues in the amino acid sequence of SEQ ID NO:1 and includes at least a portion of the amino acid residues at positions 25 to 39 in the 5 or more consecutive amino acid residues, and capable of being used as the marker for determining the risk of hyperglycemia;

(C-3) a polypeptide consisting of an amino acid sequence having 90% or more homology to an amino acid sequence that comprises 5 or more consecutive amino acid residues in the amino acid sequence of SEQ ID NO:1, and includes at least a portion of the amino acid residues at positions 25 to 39 in the 5 or more consecutive amino acid residues, and capable of being used as the marker for determining the risk of hyperglycemia;

(C-4) a polypeptide comprising an amino acid sequence having 90% or more homology to 5 or more consecutive amino acid residues selected from the amino acid residues at positions 25 to 39 in the amino acid sequence of SEQ ID NO:1, and capable of being used as the marker for determining the risk of hyperglycemia;

(C-5) a polypeptide consisting of an amino acid sequence having 90% or more homology to 5 or more consecutive amino acid residues selected from the amino acid residues at positions 25 to 39 in the amino acid sequence of SEQ ID NO:1, and capable of being used as the marker for determining the risk of hyperglycemia;

(C-6) a polypeptide comprising an amino acid sequence having 90% or more homology to the amino acid sequence of the amino acid residues at positions 25 to 39 in the amino acid sequence of SEQ ID NO:1, and capable of being used as the marker for determining the risk of hyperglycemia;

(C-7) a polypeptide consisting of an amino acid sequence having 90% or more homology to the amino acid sequence of the amino acid residues at positions 25 to 39 in the amino acid sequence of SEQ ID NO:1, and capable of being used as the marker for determining the risk of hyperglycemia;

(C-8) a polypeptide comprising an amino acid sequence having 90% or more homology to the amino acid sequence of SEQ ID NO:1, and capable of being used as the marker for determining the risk of hyperglycemia; and (C-9) a polypeptide consisting of an amino acid sequence having 90% or more homology to the amino acid sequence of SEQ ID NO:1, and capable of being used as the marker for determining the risk of hyperglycemia.

(1-2) Concerning (D) and (E)

In (D) and (E), the amino acid sequence of SEQ ID NO:1 is as explained in (1-1) above.

In (D) and (E), 5 or more consecutive amino acid residues in an amino acid sequence having a mutation(s) in the amino acid sequence of SEQ ID NO:1 are preferably 7 or more consecutive amino acid residues, more preferably 10 or more consecutive amino acid residues, still preferably 12 or more consecutive amino acid residues, still more preferably 14 or more consecutive amino acid residues, and particularly preferably 15 or more consecutive amino acid residues. Its upper limit is not particularly limited, and its length may be a full length of an amino acid sequence having each mutation in the amino acid sequence of SEQ ID NO:1 (141 residues) or may exceed this, but is, for example, 200 or less, 100 or less, 90 or less, 80 or less, 70 or less, 60 or less, 50 or less, 40 or less, 30 or less, or 20 or less.

(D) may be a polypeptide comprising 5 or more consecutive amino acid residues in an amino acid sequence having one or several amino acid deletions, additions, substitutions or insertions in the amino acid sequence of SEQ ID NO:1, and capable of being used as the marker for determining the risk of hyperglycemia. (D) is preferably a polypeptide consisting of 5 or more consecutive amino acid residues in an amino acid sequence having one or several amino acid deletions, additions, substitutions or insertions in the amino acid sequence of SEQ ID NO:1, and capable of being used as the marker for determining the risk of hyperglycemia.

(E) may be a polypeptide comprising 5 or more consecutive amino acid residues in an amino acid sequence having 90% or more homology to the amino acid sequence of SEQ ID NO:1, and capable of being used as the marker for determining the risk of hyperglycemia. (E) is preferably a polypeptide consisting of 5 or more consecutive amino acid residues in an amino acid sequence having 90% or more homology to the amino acid sequence of SEQ ID NO:1, and capable of being used as the marker for determining the risk of hyperglycemia.

One or more mutations of amino acid residues in (D) are the same as those described for (B) in (1-1) above.

The homology in (E) is the same as that described for (C) in (1-1) above.

The peptides included in the group consisting of (A) to (E) are preferably the peptides included in the group consisting of (A-2) to (A-7), (B-2) to (B-7) and (C-2) to (C-7), more preferably the peptides of (A-6) and (A-7) and still more preferably the peptide of (A-7).

(1-3) Concerning (F) to (H)

In (F) to (H), the amino acid sequence of SEQ ID NO:2 is an amino acid sequence encoding basic salivary proline-rich protein 2 (full length 416 amino acids) and has been registered as the accession number of P02812.3 in the database.

In (F) to (H), 5 or more consecutive amino acid residues in the amino acid sequence of SEQ ID NO:2 are preferably 10 or more consecutive amino acid residues, preferably 15 or more consecutive amino acid residues, more preferably 20 or more consecutive amino acid residues, still preferably 22 or more consecutive amino acid residues, still more preferably 23 or more consecutive amino acid residues, especially preferably 24 or more consecutive amino acid residues, and particularly preferably 25 or more consecutive amino acid residues, in the amino acid sequence of SEQ ID NO:2. Its upper limit is not particularly limited, and its length may be the full length of the amino acid sequence of SEQ ID NO:2 (416 residues) or may exceed this, but is, for example, 500 or less, 400 or less, 300 or less, 200 or less, 100 or less, 90 or less, 80 or less, 70 or less, 60 or less, 50 or less, 40 or less, or 30 or less.

In (F) to (H), the 5 or more consecutive amino acid residues in the amino acid sequence of SEQ ID NO:2 include preferably at least a portion of the amino acid residues at positions 17 to 112 in SEQ ID NO:2, and more preferably at least a portion of the amino acid residues at positions 59 to 83 in SEQ ID NO:2. The 5 or more consecutive amino acid residues correspond to, more preferably, 5 or more consecutive amino acid residues in the amino acid residues at positions 17 to 112 in SEQ ID NO:2, and still more preferably, 5 or more consecutive amino acid residues in the amino acid residues at positions 59 to 83 in SEQ ID NO:2. The amino acid residues at positions 17 to 112 correspond to basic proline-rich peptide IB-1. The 5 or more consecutive amino acid residues correspond to preferably the amino acid sequence of the amino acid residues at positions 59 to 83 in SEQ ID NO:2, the amino acid sequence of the amino acid residues at positions 17 to 112 in SEQ ID NO:2 or the amino acid sequence of SEQ ID NO:2, more preferably the amino acid sequence of the amino acid residues at positions 59 to 83 in SEQ ID NO:2 or the amino acid sequence of the amino acid residues at positions 17 to 112 in SEQ ID NO:2; and still more preferably the amino acid sequence of the amino acid residues at positions 59 to 83 in SEQ ID NO:2.

(F) may be a polypeptide comprising 5 or more consecutive amino acid residues in the amino acid sequence of SEQ ID NO:2, and is preferably a polypeptide consisting of the 5 or more consecutive amino acid residues in the amino acid sequence of SEQ ID NO:2.

(G) may be a polypeptide comprising an amino acid sequence having one or several amino acid deletions, additions, substitutions or insertions in 5 or more consecutive amino acid residues in the amino acid sequence of SEQ ID NO:2 and capable of being used as the marker for determining the risk of hyperglycemia. (G) is preferably a polypeptide consisting of an amino acid sequence having one or several amino acid deletions, additions, substitutions or insertions in 5 or more consecutive amino acid residues in the amino acid sequence of SEQ ID NO:2 and capable of being used as the marker for determining the risk of hyperglycemia.

(H) may be a polypeptide comprising an amino acid sequence having 90% or more homology to 5 or more consecutive amino acid residues in the amino acid sequence of SEQ ID NO:2 and capable of being used as the marker for determining the risk of hyperglycemia. (H) is preferably a polypeptide consisting of an amino acid sequence having 90% or more homology to 5 or more consecutive amino acid residues in the amino acid sequence of SEQ ID NO:2 and capable of being used as the marker for determining the risk of hyperglycemia.

In (G), one or several mutations of amino acid residues may be present in one region or in multiple different regions in the amino acid sequence. The term "one or several" denotes a range in which the function or the property of the marker peptide is not largely impaired. "One or several" refers to, for example, "1 to 41", "1 to 35", "1 to 30", "1 to 25", "1 to 20", "1 to 15", "1 to 10", "1 to 7", "1 to 5", "1 to 3", "1 to 2" or "1". Definitions and specific examples of positions and substitutions for mutation permitted to the amino acids are the same as those described for (A).

The homology in (H) is the same as that described for (C) in (1-1) above.

Examples of (F) may include (F-1) to (F-15):

(F-1) a polypeptide consisting of 5 or more consecutive amino acid residues in the amino acid sequence of SEQ ID NO:2;

(F-2) a polypeptide comprising 5 or more consecutive amino acid residues in the amino acid sequence of SEQ ID NO:2, and wherein the 5 or more consecutive amino acid residues include at least a portion of the amino acid residues at positions 59 to 83 in SEQ ID NO:2;

(F-3) a polypeptide consisting of 5 or more consecutive amino acid residues in the amino acid sequence of SEQ ID NO:2, wherein the 5 or more consecutive amino acid residues include at least a portion of the amino acid residues at positions 59 to 83 in SEQ ID NO:2;

(F-4) a polypeptide comprising 5 or more consecutive amino acid residues selected from the amino acid residues at positions 59 to 83 in the amino acid sequence of SEQ ID NO:2;

(F-5) a polypeptide consisting of 5 or more consecutive amino acid residues selected from the amino acid residues at positions 59 to 83 in the amino acid sequence of SEQ ID NO:2;

(F-6) a polypeptide comprising the amino acid residues at positions 59 to 83 in the amino acid sequence of SEQ ID NO:2;

(F-7) a polypeptide consisting of the amino acid residues at positions 59 to 83 in the amino acid sequence of SEQ ID NO:2;

(F-8) a polypeptide comprising 5 or more consecutive amino acid residues in the amino acid sequence of SEQ ID NO:2, wherein the 5 or more consecutive amino acid residues include at least a portion of the amino acid residues at positions 17 to 112 in SEQ ID NO:2;

(F-9) a polypeptide consisting of 5 or more consecutive amino acid residues in the amino acid sequence of SEQ ID NO:2, wherein the 5 or more consecutive amino acid residues include at least a portion of the amino acid residues at positions 17 to 112 in SEQ ID NO:2;

(F-10) a polypeptide comprising 5 or more consecutive amino acid residues selected from the amino acid residues at positions 17 to 112 in the amino acid sequence of SEQ ID NO:2;

(F-11) a polypeptide consisting of 5 or more consecutive amino acid residues selected from the amino acid residues at positions 17 to 112 in the amino acid sequence of SEQ ID NO:2;

(F-12) a polypeptide comprising the amino acid residues at positions 17 to 112 in the amino acid sequence of SEQ ID NO:2;

(F-13) a polypeptide consisting of the amino acid residues at positions 17 to 112 in the amino acid sequence of SEQ ID NO:2;

(F-14) a polypeptide comprising the amino acid sequence of SEQ ID NO:2; and (F-15) a polypeptide consisting of the amino acid sequence of SEQ ID NO:2.

Examples of (G) may include (G-1) to (G-15):

(G-1) a polypeptide consisting of an amino acid sequence having one or several amino acid deletions, additions, substitutions or insertions in 5 or more consecutive amino acid residues in the amino acid sequence of SEQ ID NO:2, and capable of being used as a marker for determining a risk of hyperglycemia;

(G-2) a polypeptide comprising an amino acid sequence having one or several amino acid deletions, additions, substitutions or insertions in an amino acid sequence that comprises 5 or more consecutive amino acid residues in the amino acid sequence of SEQ ID NO:2 and includes at least a portion of the amino acid residues at positions 59 to 83 in the 5 or more consecutive amino acid residues, and capable of being used as the marker for determining the risk of hyperglycemia;

(G-3) a polypeptide consisting of an amino acid sequence having one or several amino acid deletions, additions, substitutions or insertions in an amino acid sequence that comprises 5 or more consecutive amino acid residues in the amino acid sequence of SEQ ID NO:2 and includes at least a portion of the amino acid residues at positions 59 to 83 in the 5 or more consecutive amino acid residues, and capable of being used as the marker for determining the risk of hyperglycemia;

(G-4) a polypeptide comprising an amino acid sequence having one or several amino acid deletions, additions, substitutions or insertions in 5 or more consecutive amino acid residues selected from the amino acid residues at positions 59 to 83 in the amino acid sequence of SEQ ID NO:2, and capable of being used as the marker for determining the risk of hyperglycemia;

(G-5) a polypeptide consisting of an amino acid sequence having one or several amino acid deletions, additions, substitutions or insertions in 5 or more consecutive amino acid residues selected from the amino acid residues at positions 59 to 83 in the amino acid sequence of SEQ ID NO:2, and capable of being used as the marker for determining the risk of hyperglycemia;

(G-6) a polypeptide comprising an amino acid sequence having one or several amino acid deletions, additions, substitutions or insertions in the amino acid sequence of the amino acid residues at positions 59 to 83 in the amino acid sequence of SEQ ID NO:2, and capable of being used as the marker for determining the risk of hyperglycemia;

(G-7) a polypeptide consisting of an amino acid sequence having one or several amino acid deletions, additions, substitutions or insertions in the amino acid sequence of the amino acid residues at positions 59 to 83 in the amino acid sequence of SEQ ID NO:2, and capable of being used as the marker for determining the risk of hyperglycemia;

(G-8) a polypeptide comprising an amino acid sequence having one or several amino acid deletions, additions, substitutions or insertions in an amino acid sequence that comprises 5 or more consecutive amino acid residues in the amino acid sequence of SEQ ID NO:2 and includes at least a portion of the amino acid residues at positions 17 to 112 in the 5 or more consecutive amino acid residues, and capable of being used as the marker for determining the risk of hyperglycemia;

(G-9) a polypeptide consisting of an amino acid sequence having one or several amino acid deletions, additions, substitutions or insertions in an amino acid sequence that comprises 5 or more consecutive amino acid residues in the amino acid sequence of SEQ ID NO:2, and includes at least a portion of the amino acid residues at positions 17 to 112 in the 5 or more consecutive amino acid residues, and capable of being used as the marker for determining the risk of hyperglycemia;

(G-10) a polypeptide comprising an amino acid sequence having one or several amino acid deletions, additions, substitutions or insertions in 5 or more consecutive amino acid residues selected from the amino acid residues at positions 17 to 112 in the amino acid sequence of SEQ ID NO:2, and capable of being used as the marker for determining the risk of hyperglycemia;

(G-11) a polypeptide consisting of an amino acid sequence having one or several amino acid deletions, additions, substitutions or insertions in 5 or more consecutive amino acid residues selected from the amino acid residues at positions 17 to 112 in the amino acid sequence of SEQ ID NO:2, and capable of being used as the marker for determining the risk of hyperglycemia;

(G-12) a polypeptide comprising an amino acid sequence having one or several amino acid deletions, additions, substitutions or insertions in the amino acid sequence of the amino acid residues at positions 17 to 112 in the amino acid sequence of SEQ ID NO:2, and capable of being used as the marker for determining the risk of hyperglycemia;

(G-13) a polypeptide consisting of an amino acid sequence having one or several amino acid deletions, additions, substitutions or insertions in the amino acid sequence of the amino acid residues at positions 17 to 112 in the amino acid sequence of SEQ ID NO:2, and capable of being used as the marker for determining the risk of hyperglycemia;

(G-14) a polypeptide comprising an amino acid sequence having one or several amino acid deletions, additions, substitutions or insertions in the amino acid sequence of SEQ ID NO:2, and capable of being used as the marker for determining the risk of hyperglycemia; and (G-15) a polypeptide consisting of an amino acid sequence having one or several amino acid deletions, additions, substitutions or insertions in the amino acid sequence of SEQ ID NO:2, and capable of being used as the marker for determining the risk of hyperglycemia.

Examples of (H) may include (H-1) to (H-15):

(H-1) a polypeptide consisting of an amino acid sequence having 90% or more homology to 5 or more consecutive amino acid residues in the amino acid sequence of SEQ ID NO:2, and capable of being used as the marker for determining the risk of hyperglycemia;

(H-2) a polypeptide comprising an amino acid sequence having 90% or more homology to an amino acid sequence that comprises 5 or more consecutive amino acid residues in the amino acid sequence of SEQ ID NO:2 and includes at least a portion of the amino acid residues at positions 59 to 83 in the 5 or more consecutive amino acid residues, and capable of being used as the marker for determining the risk of hyperglycemia;

(H-3) a polypeptide consisting of an amino acid sequence having 90% or more homology to an amino acid sequence that comprises 5 or more consecutive amino acid residues in the amino acid sequence of SEQ ID NO:2 and includes at least a portion of the amino acid residues at positions 59 to 83 in the 5 or more consecutive amino acid residues, and capable of being used as the marker for determining the risk of hyperglycemia;

(H-4) a polypeptide comprising an amino acid sequence having 90% or more homology to 5 or more consecutive amino acid residues selected from the amino acid residues at positions 59 to 83 in the amino acid sequence of SEQ ID NO:2, and capable of being used as the marker for determining the risk of hyperglycemia;

(H-5) a polypeptide consisting of an amino acid sequence having 90% or more homology to 5 or more consecutive amino acid residues selected from the amino acid residues at positions 59 to 83 in the amino acid sequence of SEQ ID NO:2, and capable of being used as the marker for determining the risk of hyperglycemia;

(H-6) a polypeptide comprising an amino acid sequence having 90% or more homology to the amino acid sequence of the amino acid residues at positions 59 to 83 in the amino acid sequence of SEQ ID NO:2, and capable of being used as the marker for determining the risk of hyperglycemia;

(H-7) a polypeptide consisting of an amino acid sequence having 90% or more homology to the amino acid sequence of the amino acid residues at positions 59 to 83 in the amino acid sequence of SEQ ID NO:2, and capable of being used as the marker for determining the risk of hyperglycemia;

(H-8) a polypeptide comprising an amino acid sequence having 90% or more homology to an amino acid sequence that comprises 5 or more consecutive amino acid residues in the amino acid sequence of SEQ ID NO:2 and includes at least a portion of the amino acid residues at positions 17 to 112 in the 5 or more consecutive amino acid residues, and capable of being used as the marker for determining the risk of hyperglycemia;

(H-9) a polypeptide consisting of an amino acid sequence having 90% or more homology to an amino acid sequence that comprises 5 or more consecutive amino acid residues in the amino acid sequence of SEQ ID NO:2 and includes at least a portion of the amino acid residues at positions 17 to 112 in the 5 or more consecutive amino acid residues, and capable of being used as the marker for determining the risk of hyperglycemia;

(H-10) a polypeptide comprising an amino acid sequence having 90% or more homology to 5 or more consecutive amino acid residues selected from the amino acid residues at positions 17 to 112 in the amino acid sequence of SEQ ID NO:2, and capable of being used as the marker for determining the risk of hyperglycemia;

(H-11) a polypeptide consisting of an amino acid sequence having 90% or more homology to 5 or more consecutive amino acid residues selected from the amino acid residues at positions 17 to 112 in the amino acid sequence of SEQ ID NO:2, and capable of being used as the marker for determining the risk of hyperglycemia;

(H-12) a polypeptide comprising an amino acid sequence having 90% or more homology to the amino acid sequence of the amino acid residues at positions 17 to 112 in the amino acid sequence of SEQ ID NO:2, and capable of being used as the marker for determining the risk of hyperglycemia;

(H-13) a polypeptide consisting of an amino acid sequence having 90% or more homology to the amino acid sequence of the amino acid residues at positions 17 to 112 in the amino acid sequence of SEQ ID NO:2, and capable of being used as the marker for determining the risk of hyperglycemia;

(H-14) a polypeptide comprising an amino acid sequence having 90% or more homology to the amino acid sequence of SEQ ID NO:2, and capable of being used as the marker for determining the risk of hyperglycemia; and (H-15) a polypeptide consisting of an amino acid sequence having 90% or more homology to the amino acid sequence of SEQ ID NO:2, and capable of being used as the marker for determining the risk of hyperglycemia.

(1-4) Concerning (I) and (J)

In (I) and (J), the amino acid sequence of SEQ ID NO:2 is as explained in (1-3) above.

In (I) and (J), 5 or more consecutive amino acid residues in an amino acid sequence having a mutation(s) in the amino acid sequence of SEQ ID NO:2 are preferably 10 or more amino consecutive acid residues, preferably 15 or more consecutive amino acid residues, more preferably 20 or more consecutive amino acid residues, still preferably 22 or more consecutive amino acid residues, still more preferably 23 or more consecutive amino acid residues, especially preferably 24 or more consecutive amino acid residues, and particularly preferably 25 or more consecutive amino acid residues, in the amino acid sequence of SEQ ID NO:2. Its upper limit is not particularly limited, and its length may be the full length of the amino acid sequence of SEQ ID NO:2 (416 residues) or may exceed this, but is, for example, 500 or less, 400 or less, 300 or less, 200 or less, 100 or less, 90 or less, 80 or less, 70 or less, 60 or less, 50 or less, 40 or less, or 30 or less.

(I) may be a polypeptide comprising 5 or more consecutive amino acid residues in an amino acid sequence having one or several amino acid deletions, additions, substitutions or insertions in the amino acid sequence of SEQ ID NO:2, and capable of being used as the marker for determining the risk of hyperglycemia. (I) is preferably a polypeptide consisting of 5 or more consecutive amino acid residues in an amino acid sequence having one or several amino acid deletions, additions, substitutions or insertions in the amino acid sequence of SEQ ID NO:2, and capable of being used as the marker for determining the risk of hyperglycemia.

(J) may be a polypeptide comprising 5 or more consecutive amino acid residues in an amino acid sequence having 90% or more homology to the amino acid sequence of SEQ ID NO:2, and capable of being used as the marker for determining the risk of hyperglycemia. (J) is preferably a polypeptide consisting of 5 or more consecutive amino acid residues in an amino acid sequence having 90% or more homology to the amino acid sequence of SEQ ID NO:2, and capable of being used as the marker for determining the risk of hyperglycemia.

One or several mutations of amino acid residues in (I) are the same as those described for (G) in (1-3) above.

The homology in (J) is the same as that described for (C) in (1-1) above.

The peptides selected from the group consisting of (F) to (J) are preferably the peptides included in the group consisting of (F-2) to (F-13), (G-2) to (G-13) and (H-2) to (H-13), more preferably the peptides included in the group consisting of (F-6), (F-7), (G-6), (G-7), (H-6) and (H-7), and still preferably the peptides selected from the group consisting of (F-7), (G-7) and (H-7), and still more preferably the peptide of (F-7).

(1-5) Concerning (K) to (M)

In (K) to (M), the amino acid sequence of SEQ ID NO:3 is an amino acid sequence encoding basic salivary proline-rich protein 1 (full length 392 amino acids), and has been registered as the accession number of P04280.2 in the database.

In (K) to (M), 5 or more consecutive amino acid residues in the amino acid sequence of SEQ ID NO:3 are preferably 6 or more consecutive amino acid residues, and more preferably 7 or more consecutive amino acid residues, in the amino acid sequence of SEQ ID NO:3. Its upper limit is not particularly limited, and its length may be the full length of the amino acid sequence of SEQ ID NO:3 (392 residues) or may exceed this, but is, for example, 500 or less, 400 or less, 300 or less, 200 or less, 100 or less, 90 or less, 80 or less, 70 or less, 60 or less, 50 or less, 40 or less, 30 or less, 20 or less, or 10 or less.

In (K) to (M), the 5 or more consecutive amino acid residues in the amino acid sequence of SEQ ID NO:3 include: preferably at least a portion of the amino acid residues at positions 275 to 392 in SEQ ID NO:3; and more preferably at least a portion of the amino acid residues at positions 337 to 343 in SEQ ID NO:3. The 5 or more consecutive amino acid residues correspond to, still preferably, 5 or more consecutive amino acid residues in the amino acid residues at positions 275 to 392 in SEQ ID NO:3, and still more preferably, 5 or more consecutive amino acid residues in the amino acid residues at positions 337 to 343 in SEQ ID NO:3. The amino acid sequence of the amino acid residues at positions 275 to 392 in SEQ ID NO:3 corresponds to basic peptide IB-6. The 5 or more consecutive amino acid residues correspond to: preferably an amino acid sequence of the amino acid residues at positions 337 to 343 in SEQ ID NO:3, the amino acid sequence of the amino acid residues at positions 275 to 392 in SEQ ID NO:3 or the amino acid sequence of SEQ ID NO:3; more preferably the amino acid sequence of the amino acid residues at positions 337 to 343 in SEQ ID NO:3 or the amino acid sequence of the amino acid residues at positions 275 to 392 in SEQ ID NO:3; and still more preferably the amino acid sequence of the amino acid residues at positions 337 to 343 in SEQ ID NO:3.

(K) may be a polypeptide comprising 5 or more consecutive amino acid residues in the amino acid sequence of SEQ ID NO:3, and is preferably a polypeptide consisting of the 5 or more consecutive amino acid residues in the amino acid sequence of SEQ ID NO:3.

(L) may be a polypeptide comprising an amino acid sequence having one or several amino acid deletions, additions, substitutions or insertions in 5 or more consecutive amino acid residues in the amino acid sequence of SEQ ID NO:3, and capable of being used as the marker for determining the risk of hyperglycemia. (L) is preferably a polypeptide consisting of an amino acid sequence having one or several amino acid deletions, additions, substitutions or insertions in 5 or more consecutive amino acid residues in the amino acid sequence of SEQ ID NO:3, and capable of being used as a marker for determining a risk of hyperglycemia.

(M) may be a polypeptide comprising an amino acid sequence having 90% or more homology to 5 or more consecutive amino acid residues in the amino acid sequence of SEQ ID NO:3, and capable of being used as the marker for determining the risk of hyperglycemia. (M) is preferably a polypeptide consisting of an amino acid sequence having 90% or more homology to 5 or more consecutive amino acid residues in the amino acid sequence of SEQ ID NO:3, and capable of being used as the marker for determining the risk of hyperglycemia.

In (L), one or several mutations of amino acid residues may be present in one region or in multiple different regions in the amino acid sequence. The term "one or several" denotes a range in which the function or the property of the marker peptide is not largely impaired. "One or several" refers to, for example, "1 to 39", "1 to 35", "1 to 30", "1 to 25", "1 to 20", "1 to 15", "1 to 10", "1 to 7", "1 to 5", "1 to 3", "1 to 2" or "1". Definitions and specific examples of positions and substitutions for mutation permitted to the amino acids are the same as those described for (A).

The homology in (M) is the same as that described for (C) in (1-1) above.

Examples of (K) may include (K-1) to (K-15):

(K-1) a polypeptide consisting of 5 or more consecutive amino acid residues in the amino acid sequence of SEQ ID NO:3;

(K-2) a polypeptide comprising 5 or more consecutive amino acid residues in the amino acid sequence of SEQ ID NO:3, wherein the 5 or more consecutive amino acid residues include at least a portion of the amino acid residues at positions 337 to 343 in SEQ ID NO:3;

(K-3) a polypeptide consisting of 5 or more consecutive amino acid residues in the amino acid sequence of SEQ ID NO:3, wherein the 5 or more consecutive amino acid residues include at least a portion of the amino acid residues at positions 337 to 343 in SEQ ID NO:3;

(K-4) a polypeptide comprising 5 or more consecutive amino acid residues selected from the amino acid residues at positions 337 to 343 in the amino acid sequence of SEQ ID NO:3;

(K-5) a polypeptide consisting of 5 or more consecutive amino acid residues selected from the amino acid residues at positions 337 to 343 in the amino acid sequence of SEQ ID NO:3;

(K-6) a polypeptide comprising the amino acid residues at positions 337 to 343 in the amino acid sequence of SEQ ID NO:3;

(K-7) a polypeptide consisting of the amino acid residues at positions 337 to 343 in the amino acid sequence of SEQ ID NO:3;

(K-8) a polypeptide comprising 5 or more consecutive amino acid residues in the amino acid sequence of SEQ ID NO:3, wherein the 5 or more consecutive amino acid residues include at least a portion of the amino acid residues at positions 275 to 392 in SEQ ID NO:3;

(K-9) a polypeptide consisting of 5 or more consecutive amino acid residues in the amino acid sequence of SEQ ID NO:3, wherein the 5 or more consecutive amino acid residues include at least a portion of the amino acid residues at positions 275 to 392 in SEQ ID NO:3;

(K-10) a polypeptide comprising 5 or more consecutive amino acid residues selected from the amino acid residues at positions 275 to 392 in the amino acid sequence of SEQ ID NO:3;

(K-11) a polypeptide consisting of 5 or more consecutive amino acid residues selected from the amino acid residues at positions 275 to 392 in the amino acid sequence of SEQ ID NO:3;

(K-12) a polypeptide comprising the amino acid residues at positions 275 to 392 in the amino acid sequence of SEQ ID NO:3;

(K-13) a polypeptide consisting of the amino acid residues at positions 275 to 392 in the amino acid sequence of SEQ ID NO:3;

(K-14) a polypeptide comprising the amino acid sequence of SEQ ID NO:3; and (K-15) a polypeptide consisting of the amino acid sequence of SEQ ID NO:3.

Examples of (L) may include (L-1) to (L-15):

(L-1) a polypeptide consisting of an amino acid sequence having one or several amino acid deletions, additions, substitutions or insertions in 5 or more consecutive amino acid residues in the amino acid sequence of SEQ ID NO:3, and capable of being used as the marker for determining the risk of hyperglycemia;

(L-2) a polypeptide comprising an amino acid sequence having one or several amino acid deletions, additions, substitutions or insertions in an amino acid sequence that comprises 5 or more consecutive amino acid residues in the amino acid sequence of SEQ ID NO:3 and includes at least a portion of the amino acid residues at positions 337 to 343 in the 5 or more consecutive amino acid residues, and capable of being used as the marker for determining the risk of hyperglycemia;

(L-3) a polypeptide consisting of an amino acid sequence having one or several amino acid deletions, additions, substitutions or insertions in an amino acid sequence that comprises 5 or more consecutive amino acid residues in the amino acid sequence of SEQ ID NO:3 and includes at least a portion of the amino acid residues at positions 337 to 343 in the 5 or more consecutive amino acid residues, and capable of being used as the marker for determining the risk of hyperglycemia;

(L-4) a polypeptide comprising an amino acid sequence having one or several amino acid deletions, additions, substitutions or insertions in 5 or more consecutive amino acid residues selected from the amino acid residues at positions 337 to 343 in the amino acid sequence of SEQ ID NO:3, and capable of being used as the marker for determining the risk of hyperglycemia;

(L-5) a polypeptide consisting of an amino acid sequence having one or several amino acid deletions, additions, substitutions or insertions in 5 or more consecutive amino acid residues selected from the amino acid residues at positions 337 to 343 in the amino acid sequence of SEQ ID NO:3, and capable of being used as the marker for determining the risk of hyperglycemia;

(L-6) a polypeptide comprising an amino acid sequence having one or several amino acid deletions, additions, substitutions or insertions in the amino acid sequence of the amino acid residues at positions 337 to 343 in the amino acid sequence of SEQ ID NO:3, and capable of being used as the marker for determining the risk of hyperglycemia;

(L-7) a polypeptide consisting of an amino acid sequence having one or several amino acid deletions, additions, substitutions or insertions in the amino acid sequence of the amino acid residues at positions 337 to 343 in the amino acid sequence of SEQ ID NO:3, and capable of being used as the marker for determining the risk of hyperglycemia;

(L-8) a polypeptide comprising an amino acid sequence having one or several amino acid deletions, additions, substitutions or insertions in an amino acid sequence that comprises 5 or more consecutive amino acid residues in the amino acid sequence of SEQ ID NO:3, and includes at least a portion of the amino acid residues at positions 275 to 392 in the 5 or more consecutive amino acid residues, and capable of being used as the marker for determining the risk of hyperglycemia;

(L-9) a polypeptide consisting of an amino acid sequence having one or several amino acid deletions, additions, substitutions or insertions in an amino acid sequence that comprises 5 or more consecutive amino acid residues in the amino acid sequence of SEQ ID NO:3 and includes at least a portion of the amino acid residues at positions 275 to 392 in the 5 or more consecutive amino acid residues, and capable of being used as the marker for determining the risk of hyperglycemia;

(L-10) a polypeptide comprising an amino acid sequence having one or several amino acid deletions, additions, substitutions or insertions in 5 or more consecutive amino acid residues selected from the amino acid residues at positions 275 to 392 in the amino acid sequence of SEQ ID NO:3, and capable of being used as the marker for determining the risk of hyperglycemia;

(L-11) a polypeptide consisting of an amino acid sequence having one or several amino acid deletions, additions, substitutions or insertions in 5 or more consecutive amino acid residues selected from the amino acid residues at positions 275 to 392 in the amino acid sequence of SEQ ID NO:3, and capable of being used as the marker for determining the risk of hyperglycemia;

(L-12) a polypeptide comprising an amino acid sequence having one or several amino acid deletions, additions, substitutions or insertions in the amino acid sequence of the amino acid residues at positions 275 to 392 in the amino acid sequence of SEQ ID NO:3, and capable of being used as the marker for determining the risk of hyperglycemia;

(L-13) a polypeptide consisting of an amino acid sequence having one or several amino acid deletions, additions, substitutions or insertions in the amino acid sequence of the amino acid residues at positions 275 to 392 in the amino acid sequence of SEQ ID NO:3, and capable of being used as the marker for determining the risk of hyperglycemia;

(L-14) a polypeptide comprising an amino acid sequence having one or several amino acid deletions, additions, substitutions or insertions in the amino acid sequence of SEQ ID NO:3, and capable of being used as the marker for determining the risk of hyperglycemia; and (L-15) a polypeptide consisting of an amino acid sequence having one or several amino acid deletions, additions, substitutions or insertions in the amino acid sequence of SEQ ID NO:3, and capable of being used as the marker for determining the risk of hyperglycemia.

Examples of (M) may include (M-1) to (M-15):

(M-1) a polypeptide consisting of an amino acid sequence having 90% or more homology to 5 or more consecutive amino acid residues in the amino acid sequence of SEQ ID NO:3, and capable of being used as the marker for determining the risk of hyperglycemia;

(M-2) a polypeptide comprising an amino acid sequence having 90% or more homology to an amino acid sequence that comprises 5 or more consecutive amino acid residues in the amino acid sequence of SEQ ID NO:3 and includes at least a portion of the amino acid residues at positions 337 to 343 in the 5 or more consecutive amino acid residues, and capable of being used as the marker for determining the risk of hyperglycemia;

(M-3) a polypeptide consisting of an amino acid sequence having 90% or more homology to an amino acid sequence that comprises 5 or more consecutive amino acid residues in the amino acid sequence of SEQ ID NO:3 and includes at least a portion of the amino acid residues at positions 337 to 343 in the 5 or more consecutive amino acid residues, and capable of being used as the marker for determining the risk of hyperglycemia;

(M-4) a polypeptide comprising an amino acid sequence having 90% or more homology to 5 or more consecutive amino acid residues selected from the amino acid residues at positions 337 to 343 in the amino acid sequence of SEQ ID NO:3, and capable of being used as the marker for determining the risk of hyperglycemia;

(M-5) a polypeptide consisting of an amino acid sequence having 90% or more homology to 5 or more consecutive amino acid residues selected from the amino acid residues at positions 337 to 343 in the amino acid sequence of SEQ ID NO:3, and capable of being used as the marker for determining the risk of hyperglycemia;

(M-6) a polypeptide comprising an amino acid sequence having 90% or more homology to the amino acid sequence of the amino acid residues at positions 337 to 343 in the amino acid sequence of SEQ ID NO:3, and capable of being used as the marker for determining the risk of hyperglycemia;

(M-7) a polypeptide consisting of an amino acid sequence having 90% or more homology to the amino acid sequence of the amino acid residues at positions 337 to 343 in the amino acid sequence of SEQ ID NO:3, and capable of being used as the marker for determining the risk of hyperglycemia;

(M-8) a polypeptide comprising an amino acid sequence having 90% or more homology to an amino acid sequence that comprises 5 or more consecutive amino acid residues in the amino acid sequence of SEQ ID NO:3 and includes at least a portion of the amino acid residues at positions 275 to 392 in the 5 or more consecutive amino acid residues, and capable of being used as the marker for determining the risk of hyperglycemia;

(M-9) a polypeptide consisting of an amino acid sequence having 90% or more homology to an amino acid sequence that comprises 5 or more consecutive amino acid residues in the amino acid sequence of SEQ ID NO:3 and includes at least a portion of the amino acid residues at positions 275 to 392 in the 5 or more consecutive amino acid residues, and capable of being used as the marker for determining the risk of hyperglycemia;

(M-10) a polypeptide comprising an amino acid sequence having 90% or more homology to 5 or more consecutive amino acid residues selected from the amino acid residues at positions 275 to 392 in the amino acid sequence of SEQ ID NO:3 and capable of being used as the marker for determining the risk of hyperglycemia;

(M-11) a polypeptide consisting of an amino acid sequence having 90% or more homology to 5 or more consecutive amino acid residues selected from the amino acid residues at positions 275 to 392 in the amino acid sequence of SEQ ID NO:3, and capable of being used as the marker for determining the risk of hyperglycemia;

(M-12) a polypeptide comprising an amino acid sequence having 90% or more homology to the amino acid sequence of the amino acid residues at positions 275 to 392 in the amino acid sequence of SEQ ID NO:3, and capable of being used as the marker for determining the risk of hyperglycemia;

(M-13) a polypeptide consisting of an amino acid sequence having 90% or more homology to the amino acid sequence of the amino acid residues at positions 275 to 392 in the amino acid sequence of SEQ ID NO:3, and capable of being used as the marker for determining the risk of hyperglycemia;

(M-14) a polypeptide comprising an amino acid sequence having 90% or more homology to the amino acid sequence of SEQ ID NO:3, and capable of being used as the marker for determining the risk of hyperglycemia; and (M-15) a polypeptide consisting of an amino acid sequence having 90% or more homology to the amino acid sequence of SEQ ID NO:3, and capable of being used as the marker for determining the risk of hyperglycemia.

(1-6) Concerning (N) and (O)

In (N) and (O), the amino acid sequence of SEQ ID NO:3 is as described in (1-5) above.

In (N) and (O), 5 or more consecutive amino acid residues in an amino acid sequence having a mutation(s) in the amino acid sequence of SEQ ID NO:3 are preferably 6 or more consecutive amino acid residues, and more preferably 7 or more amino consecutive acid residues, in the amino acid sequence of SEQ ID NO:3. Its upper limit is not particularly limited, and its length may be the full length of the amino acid sequence of SEQ ID NO:3 (392 residues) or may exceed this, but is, for example, 500 or less, 400 or less, 300 or less, 200 or less, 100 or less, 90 or less, 80 or less, 70 or less, 60 or less, 50 or less, 40 or less, 30 or less, 20 or less, or 10 or less.

(N) may be a polypeptide comprising 5 or more consecutive amino acid residues in an amino acid sequence having one or several amino acid deletions, additions, substitutions or insertions in the amino acid sequence of SEQ ID NO:3, and capable of being used as the marker for determining the risk of hyperglycemia. (N) is preferably a polypeptide consisting of 5 or more consecutive amino acid residues in an amino acid sequence having one or several amino acid deletions, additions, substitutions or insertions in the amino acid sequence of SEQ ID NO:3, and capable of being used as the marker for determining the risk of hyperglycemia.

(O) may be a polypeptide comprising 5 or more consecutive amino acid residues in an amino acid sequence having 90% or more homology to the amino acid sequence of SEQ ID NO:3, and capable of being used as the marker for determining the risk of hyperglycemia. (O) is preferably a polypeptide consisting of 5 or more consecutive amino acid residues in an amino acid sequence having 90% or more homology to the amino acid sequence of SEQ ID NO:3, and capable of being used as the marker for determining the risk of hyperglycemia.

One or several mutations of amino acid residues in (N) are the same as those described for (L) in (1-5) above.

The homology in (O) is the same as that described for (C) in (1-1) above.

The peptides selected from the group consisting of (K) to (O) are preferably the peptides included in the group consisting of (K-2) to (K-13), (L-2) to (L-13) and (M-2) to (M-13), more preferably the peptides included in the group consisting of (K-6), (K-7), (L-6), (L-7), (M-6) and (M-7), still preferably the peptides selected from the group consisting of (K-7), (L-7) and (M-7), and still more preferably the peptide of (K-7).

(2) Antibody or Aptamer of the Present Invention

An antibody or an aptamer of the present invention is an antibody or an aptamer that is bound to the marker peptide for determining the risk of hyperglycemia of the present invention.

By the use of the antibody or the aptamer of the present invention, an amount or the presence/absence of the marker peptide for determining a risk of hyperglycemia of the present invention can be measured, and it is possible to determine the risk of hyperglycemia. That is, it is determined that the risk of hyperglycemia is high, if the amount of the marker peptide bound to the antibody or the aptamer of the present invention when a biological sample collected from a subject is allowed to act upon the antibody or the aptamer is less than the amount of the marker peptide bound to the antibody or the aptamer when a biological sample collected from a healthy donor is allowed to act upon the antibody or the aptamer.

The antibody or the aptamer may be made by standard methods.

An example when the amount or the presence/absence of the peptide is measured using the antibody or the aptamer of the present invention is shown below. First, the antibody or the aptamer is adsorbed to a carrier such as a microtiter plate by a known method such as physical adsorption, covalent binding utilizing a functional group, subsequently a biological sample is added after being diluted if necessary, and the plate is incubated. Then, a secondary antibody bound to a fluorescent substance, a chemiluminescent substance or an enzyme is added, and the mixture is incubated. After adding each substrate, detection is evaluated and determined by measuring fluorescence, chemiluminescence or visible light by an enzymatic reaction.

The marker peptide for determining the risk of hyperglycemia of the present invention is a peptide present at detectable level in a biological sample collected from a subject having the risk of hyperglycemia. Thus, the risk of hyperglycemia can be determined using the presence of the marker peptide of the present invention as an indicator.

(3) Microarray of the Present Invention

A microarray of the present invention is a microarray to which the antibody or the aptamer to be bound to the marker peptide for determining the risk of hyperglycemia described above in the present invention has been immobilized.

The microarray collectively refers to a device where a substance capable of being bound to a substance to be measured is arrayed and immobilized on a carrier (substrate). A material for the carrier on the microarray may be any of inorganic materials such as glass and organic materials such as nitrocellulose. A shape of the carrier on the microarray may be any of films, beads and plates.

The antibody or the aptamer described in the above (2) may be immobilized to a carrier to produce the microarray. Upon immobilization, an instrument such as a microarrayer or a spotter may be used.

By the use of the microarray of the present invention, an amount or the presence/absence of the marker peptide for determining a risk of hyperglycemia of the present invention can be measured, and it is possible to determine a risk of hyperglycemia. That is, it is determined that the risk of hyperglycemia is high, if the amount of the marker peptide bound to the antibody or the aptamer on the microarray of the present invention when a biological sample collected from a subject is allowed to act upon the microarray is less than the amount of the marker peptide bound to the antibody or the aptamer when a biological sample collected from a healthy donor is allowed to act upon the microarray.

An example when the amount of the peptide is determined using the microarray of the present invention is shown below. First, a biological sample is added to the antibody or the aptamer immobilized onto the microarray to couple the marker peptide in the biological sample with the antibody or the aptamer. Then, a secondary antibody bound to a fluorescent substance, a chemiluminescent substance or an enzyme is added and the mixture is incubated. After adding each substrate, detection may be carried out by measuring the fluorescence, the chemiluminescence or the visible light by the enzymatic reaction.

(4) Determination Method of the Present Invention

The method of determining the risk of hyperglycemia of the present invention is a method of measuring the amount or the presence/absence of the marker peptide for determining the risk of hyperglycemia.

When the risk of hyperglycemia is determined from the amount of marker peptide for determining the risk of hyperglycemia, generally comparison to a reference value is carried out. Examples of the reference value may include an amount of the marker peptide in a biological sample collected from a healthy donor (preferably it has been previously confirmed by a procedure other than the determination method of the present invention that the donor is certainly healthy); and an amount of the marker peptide in a biological sample collected from a donor with hyperglycemia (preferably it has been previously confirmed by a procedure other than the determination method of the present invention that the subject is certainly hyperglycemic). Of these, the former is preferable.

When the reference value is a value from the healthy donor, if the amount of the marker peptide for determining the risk of hyperglycemia in the biological sample collected from the subject is smaller than the amount of the marker peptide in the biological sample collected from the healthy donor, it is determined that the risk of hyperglycemia is high.

When the reference value is a value from the donor with hyperglycemia, if the amount of the marker peptide for determining the risk of hyperglycemia in the biological sample collected from the subject is equivalent to or smaller than the amount of the marker peptide in the biological sample collected from the donor with hyperglycemia, it is determined that the risk of hyperglycemia is high.

In the determination method of the present invention, when the amount of the marker peptide for determining the risk of hyperglycemia in the biological sample collected from the subject is smaller than the amount of the marker peptide in the biological sample collected from the healthy donor, it is determined that the risk of hyperglycemia is high. On the other hand, when the amount of the marker peptide for determining the risk of hyperglycemia in the biological sample collected from the subject is equivalent to or larger than the amount of the marker peptide in the biological sample collected from the healthy donor, it is determined that the risk of hyperglycemia is low.

Examples of the biological sample may include body fluids such as saliva, blood such as whole blood, plasma, serum, urine, tear and the like. Of these, a non-invasive and always collectable biological sample is preferable and saliva is more preferable. Saliva is also suitable as a specimen used for determining at home. Saliva includes stimulating saliva and unstimulated saliva, and stimulating saliva is preferable. Stimulating saliva can easily be collected by chewing a paraffin gum. The use of saliva makes it easy to regularly figure out a blood glucose level, and is preferable because this can lead to reduction of a morbidity of a disease such as hyperglycemia and diabetes and to maintenance of health.

In the determination method of the present invention, the amount of the marker peptide for determining the risk of hyperglycemia can be measured by, for example, an immunoassay using the above antibody or aptamer, an immunoassay using the above microarray, a mass spectrometry, RIA (radioimmunoassay), ELISA (enzyme linked immunosorbent assay), or ECLIA (electrochemical luminescence immunoassay). The immunoassay using the antibody or aptamer is as already described in (2) above. The immunoassay using the microarray is as already described in (2) above.

Upon measurement by the mass spectrometry, various mass spectrometric apparatuses can be utilized. Examples of the mass spectrometric apparatuses may include GC-MS, LC-MS, FAB-MS, EI-MS, CI-MS, FD-MS, MALDI-MS, ESI-MS, HPLC-MS, FT-ICR-MS, CE-MS, ICP-MS, Py-MS, and TOF-MS, and any of them is available.

In the determination, multivariate analysis may be carried out using amounts of two or more marker peptides for determining the risk of hyperglycemia as variables. Examples of the multivariate analysis may include logistic regression analysis, multiple regression analysis, principal component analysis, independent component analysis, factor analysis, discrimination analysis, quantification theory, cluster analysis, conjoint analysis and multidimensional scaling method (MDS), and among them the logistic regression analysis is preferable.

The determination method of the present invention is suitable for evaluating a predisposition for a hyperglycemic state in a subject. The determination method of the present invention can evaluate the presence/absence of the risk of hyperglycemia in a subject, and thus is available in a preventive manner. Further, when a therapeutic or preventive procedure for hyperglycemia is given to a subject having the risk of hyperglycemia, a risk of developing hyperglycemia or a disease with hyperglycemia (hyperglycemic disease, diabetes and the like) is prone to decrease, and the amount of the marker peptide also decreases depending on it. Therefore, by measuring the amount or the presence/absence of the marker peptide while the therapeutic or preventive procedure is given, it is also possible to evaluate and determine the therapeutic or preventive procedure, for example, as follows:

A method of determining a therapeutic or preventive procedure for hyperglycemia, wherein it is determined that the therapeutic or preventive procedure is effective in the following case (1) or (2):

(1) an amount of a marker peptide for determining a risk of hyperglycemia selected from the group consisting of (A) to (O) above is smaller than the amount of the marker peptide in a biological sample collected from a healthy donor after giving the therapeutic or preventive procedure for hyperglycemia to a subject with hyperglycemia or a subject having a risk of hyperglycemia; or (2) an amount of the marker peptide for determining the risk of hyperglycemia in a subject is equivalent to or smaller than the amount of the marker peptide in a biological sample collected from a donor with hyperglycemia after giving the therapeutic or preventive procedure for hyperglycemia to the subject with hyperglycemia or the subject having the risk of hyperglycemia.

Further also the peptide of the present invention can be a biomarker for determining a therapeutic effect or a preventive effect such as an effect of drug administration, for example, as follows:

A method of determining a therapeutic effect or a preventive effect of a drug for hyperglycemia, wherein it is determined that the drug is effective for hyperglycemia in the following case (1) or (2):

(1) an amount of a marker peptide for determining a risk of hyperglycemia selected from the group consisting of (A) to (O) above is smaller than the amount of the marker peptide in a biological sample collected from a healthy donor after administering the drug to the subject with hyperglycemia or the subject having the risk of hyperglycemia; or (2) an amount of the marker peptide for determining the risk of hyperglycemia in a subject is equivalent to or smaller than the amount of the marker peptide in a biological sample collected from a donor with hyperglycemia after administering the drug to the subject with hyperglycemia or the subject having the risk of hyperglycemia.

Likewise, the determination method of the present invention is useful as a method of determining a therapeutic effect or a preventive effect of a drug for treating hyperglycemia such as an administration effect, for example as follows:

A method of determining a therapeutic effect or a preventive effect of a drug for treating hyperglycemia wherein it is determined that the drug is effective for hyperglycemia in the following case (1) or (2):

(1) an amount of a marker peptide for determining a risk of hyperglycemia selected from the group consisting of (A) to (O) above is smaller than the amount of the marker peptide in a biological sample collected from a healthy donor after administering the drug for treating hyperglycemia to the subject with hyperglycemia or the subject having the risk of hyperglycemia; or (2) an amount of the marker peptide for determining the risk of hyperglycemia in a subject is equivalent to or smaller than the amount of the marker peptide in a biological sample collected from a donor with hyperglycemia after administering the drug for treating hyperglycemia to the subject with hyperglycemia or the subject having the risk of hyperglycemia.

The peptide of the present invention is also useful for applying as a method of inhibiting hyperglycemia, a method of treating hyperglycemia or a method of preventing hyperglycemia, for example, as follows:

A method of inhibiting hyperglycemia in a subject, comprising steps of:

measuring an amount of the marker peptide for determining a risk of hyperglycemia described in the above [1] in a subject;

administering an effective amount of one or more compounds for inhibiting an expression of the marker peptide for determining a risk of hyperglycemia described in the above [1] to the subject, and thereby altering the amount of the marker peptide expressed in vivo in the subject to reduce a blood glucose level in the subject with hyperglycemia; and altering the amount of the marker peptide expressed in vivo in the subject by administering an effective amount of one or more compounds for inhibiting the expression of the marker peptide for determining the risk of hyperglycemia described in [1] above to the subject when (1) an amount of the marker peptide for determining the risk of hyperglycemia selected from the group consisting of (A) to (O) above is smaller than the amount in a biological sample collected from a healthy donor; or (2) an amount of the marker peptide for determining a risk of hyperglycemia in the subject is equivalent to or smaller than the amount of the marker peptide in a biological sample collected from a donor with hyperglycemia.

The compound for inhibiting the expression of the marker peptide for determining a risk of hyperglycemia may inhibit an expression of the marker peptide for determining a risk of hyperglycemia, and its structure such as chemical structure and molecular weight is not particularly limited. The compounds may be one or more or two or more. The compound may be administered to a subject as a composition comprising a pharmacologically acceptable carrier. The effective amount of the compound or the composition may be an amount in which the expression of the marker peptide for determining the risk of hyperglycemia can be inhibited in the subject.

(5) Kit of the Present Invention

A kit for determining a risk of hyperglycemia of the present invention comprises the antibody or aptamer or the microarray.

Preferably, the kit of the present invention further comprises a gum. This makes it easy to collect stimulating saliva as the biological sample. The gum may be a gum such as paraffin gum generally used for collecting stimulating saliva.

EXAMPLES

Example 1

Comparison of Expressed Amounts of Each Peptide Fragment in Saliva

<Evaluation Method>
(1) Sampling of Saliva Specimens

Stimulating saliva (saliva, secretion of which is facilitated by chewing a paraffin gum) was collected from subjects having a following feature.

Hyperglycemic group: fasting blood glucose level of 110 mg/dL or more and/or hemoglobin level of 5.8% or more (n=8).

Healthy group: fasting blood glucose level of less than 110 mg/dL and/or hemoglobin level of less than 5.8% (n=32).
(2) Exhaustive Analysis of Saliva Components by Metabolome Analysis Sampled saliva was centrifuged to remove contaminants, and a supernatant was subjected to LC-MS (Positive/Negative), CE-MS (Cation/Anion). The saliva components were identified from an Rt value and a Ms value.
<Evaluation Results>

Figure 2:
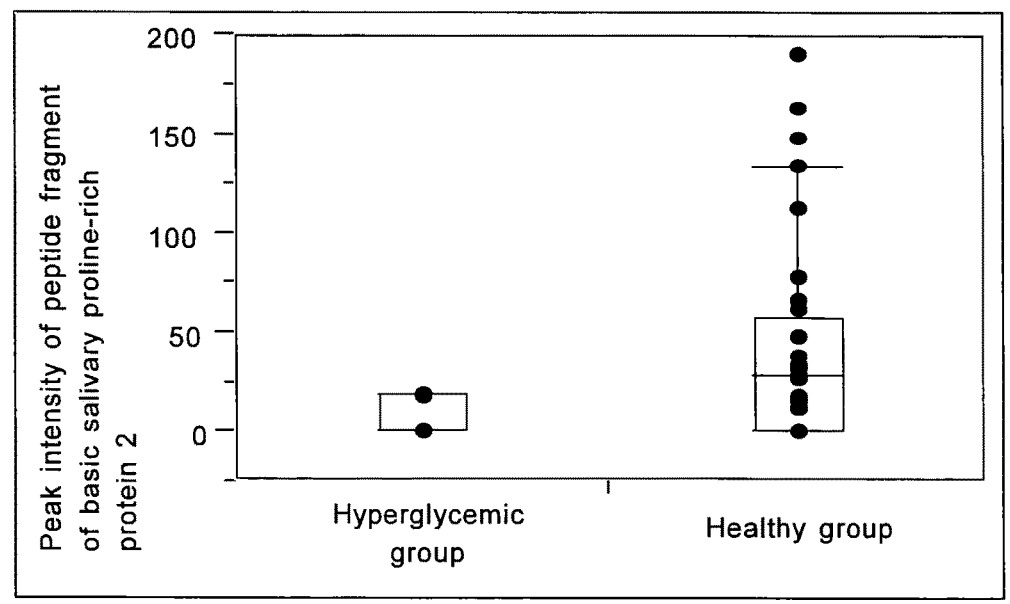
FIG. 2 indicates peak intensity of a peptide fragment of basic salivary proline-rich protein 2 in each subject group.
Figure 3:
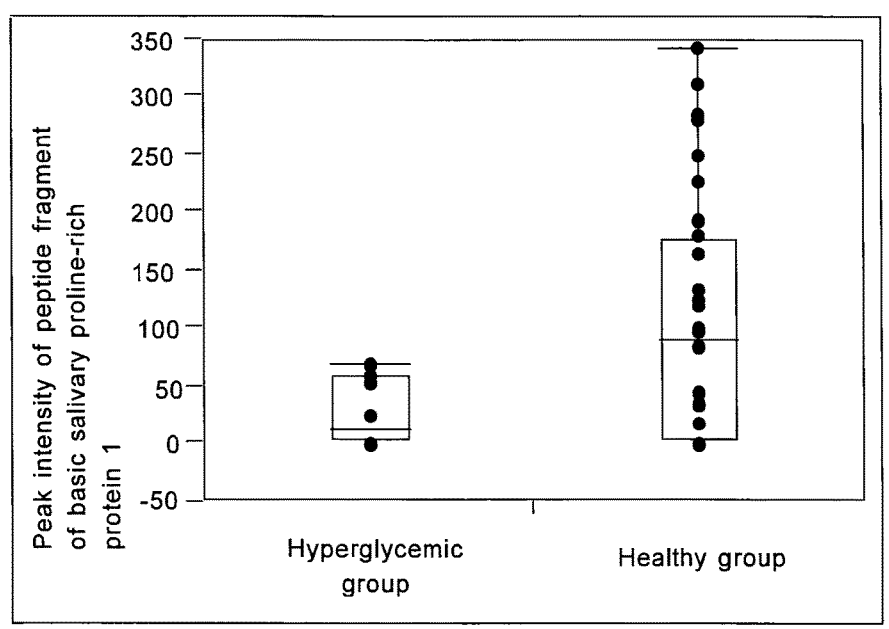
FIG. 3 indicates peak intensity of a peptide fragment of basic salivary proline-rich protein 1 in each subject group.

As a result of the metabolome analysis, it was observed that peaks corresponding to a peptide consisting of an amino acid sequence of amino acid residues at positions 25 to 39 in the amino acid sequence of SEQ ID NO:1, an amino acid sequence of amino acid residues at positions 59 to 83 in the amino acid sequence of SEQ ID NO:2, and an amino acid sequence of amino acid residues at positions 337 to 343 in the amino acid sequence of SEQ ID NO:3 were significantly reduced in the hyperglycemic group. As a result of protein database search, it was found that the amino acid sequence of SEQ ID NO:1 was the amino acid sequence of cystatin-SN, the amino acid sequence of SEQ ID NO:2 was the amino acid sequence of basic salivary proline-rich protein 2, the amino acid sequence of SEQ ID NO:3 was the amino acid sequence of basic salivary proline-rich protein 1 and the above respective peptides were fragments thereof. A peak intensity of each peptide in each group is shown in FIGS. 1 to 3 and TABLES 1 to 3. Results of tests for significant difference are shown in TABLES 1 to 3. In TABLES, the significant difference in the test is denoted by an asterisk.

Table 1. Mean of Peak Intensity and Significant Difference of Fragment from Cystatin-SN Peptide (SEQ ID NO:1) (Wilcoxon Test)

| SUBJECT GROUP | PEAK INTENSITY | SIGNIFICANT DIFFERENCE (VS HEALTHY GROUP) |
|---|---|---|
| HEALTHY GROUP | 22.6 | — |
| HYPERGLYCEMIA GROUP | 0.0 | 0.0058* |

Table 2. Mean of Peak Intensity and Significant Difference of Fragment from Basic Salivary Proline-Rich Protein 2 (SEQ ID NO:2) (Wilcoxon Test).

| SUBJECT GROUP | PEAK INTENSITY | SIGNIFICANT DIFFERENCE (VS HEALTHY GROUP) |
|---|---|---|
| HEALTHY GROUP | 42.4 | — |
| HYPERGLYCEMIA GROUP | 7.0 | 0.0350* |

Table 3. Mean of Peak Intensity and Significant Difference of Fragment from Basic Salivary Proline-Rich Protein 1 (SEQ ID NO:3) (Student's T Test).

| SUBJECT GROUP | PEAK INTENSITY | SIGNIFICANT DIFFERENCE (VS HEALTHY GROUP) |
|---|---|---|
| HEALTHY GROUP | 105.4 | — |
| HYPERGLYCEMIA GROUP | 25.4 | 0.0426* |

As shown in FIG. 1 and TABLE 1, the peak intensity of a cystatin-SN peptide fragment was shown to reduce with significant difference in the hyperglycemia group compared with the healthy group. This indicates that the risk of hyperglycemia is determined to be high when the peak intensity is below 22.6 that is the peak intensity of in the healthy group.

As shown in FIG. 2 and TABLE 2, the peak intensity of a peptide fragment of the basic salivary proline-rich peptide 2 was shown to reduce with significant difference in the hyperglycemia group compared with the healthy group. This indicates that the risk of hyperglycemia is determined to be high when the peak intensity is below 42.4 that is the peak intensity of in the healthy group.

As shown in FIG. 3 and TABLE 3, the peak intensity of a peptide fragment of the basic salivary proline-rich peptide 1 was shown to reduce with significant difference in the hyperglycemia group compared with the healthy group. This indicates that the risk of hyperglycemia is determined to be high when the peak intensity is below 105.4 that is the peak intensity of in the healthy group.

The invention claimed is:

1. A method of detecting a level of at least one peptide fragment selected from the group consisting of amino acids 25 to 39 of SEQ ID NO:1, amino acids 59 to 83 of SEQ ID NO:2, and amino acids 337-343 of SEQ ID NO:3, the method comprising:

measuring the level of the at least one peptide fragment in a sample obtained from a subject.

2. The method according to claim 1, wherein the measuring comprises measuring by a mass spectrometry; an immunoassay using an antibody or aptamer that binds to the at least one peptide fragment; or an immunoassay using a microarray wherein an antibody or an aptamer that binds to the at least one peptide fragment is immobilized on a carrier.

3. The method according to claim 1, wherein the sample is saliva.

4. The method according to claim 1, wherein the at least one peptide fragment is amino acids 25 to 39 of SEQ ID NO:1.

5. The method according to claim 1, wherein the at least one peptide fragment is amino acids 59 to 83 of SEQ ID NO:2.

6. The method according to claim 1, wherein the at least one peptide fragment is amino acids 337-343 of SEQ ID NO:3.

7. The method according to claim 1, wherein the subject is human.

8. The method according to claim 1, comprising measuring the level of at least two of the peptide fragments.

9. The method according to claim 1, wherein the subject has a risk of hyperglycemia.

10. The method according to claim 1, wherein the subject has no risk of hyperglycemia.

* * * * *